US009226507B2

(12) United States Patent
Pirotte

(10) Patent No.: US 9,226,507 B2
(45) Date of Patent: Jan. 5, 2016

(54) METHOD FOR PRODUCING EMULSIFIABLE PESTICIDE SOLUTIONS

(76) Inventor: Alan Pirotte, Houffalize (BE)

(*) Notice: Subject to any disclaimer, the term of this patent is extended or adjusted under 35 U.S.C. 154(b) by 47 days.

(21) Appl. No.: 14/233,236

(22) PCT Filed: Jul. 19, 2012

(86) PCT No.: PCT/EP2012/064237
§ 371 (c)(1),
(2), (4) Date: Jan. 16, 2014

(87) PCT Pub. No.: WO2013/011108
PCT Pub. Date: Jan. 24, 2013

(65) Prior Publication Data
US 2014/0148510 A1 May 29, 2014

(30) Foreign Application Priority Data

Jul. 19, 2011 (EP) .................................. 11174573

(51) Int. Cl.
A01N 53/00 (2006.01)
A01N 25/02 (2006.01)
A01N 25/30 (2006.01)
A01N 25/04 (2006.01)
A01N 37/42 (2006.01)

(52) U.S. Cl.
CPC .............. A01N 53/00 (2013.01); A01N 25/02 (2013.01); A01N 25/04 (2013.01); A01N 25/30 (2013.01); A01N 37/42 (2013.01)

(58) Field of Classification Search
CPC ......... A01B 53/00; A01B 25/04; A01B 37/42
USPC ....................................................... 514/521
See application file for complete search history.

(56) References Cited

U.S. PATENT DOCUMENTS

| | | | |
|---|---|---|---|
| 3,312,589 A | 4/1967 | Entley et al. | |
| 4,502,861 A | 3/1985 | Becker et al. | |
| 6,462,052 B1 | 10/2002 | Duvert et al. | |
| 2008/0182755 A1 | 7/2008 | Kozuki | |
| 2008/0274154 A1 | 11/2008 | Bussmann et al. | |
| 2009/0325808 A1 | 12/2009 | Stern et al. | |
| 2014/0148510 A1 | 5/2014 | Pirotte | |
| 2014/0193503 A1 | 7/2014 | Pirotte | |

FOREIGN PATENT DOCUMENTS

| | | |
|---|---|---|
| DE | 3248115 A1 | 6/1984 |
| EP | 0007731 | 2/1980 |
| EP | 0388239 | 9/1990 |
| EP | 1625791 A1 | 2/2006 |
| FR | 2582546 A2 | 12/1986 |
| WO | WO 2006/002984 A1 | 1/2006 |
| WO | WO 2007/017501 A2 | 2/2007 |
| WO | WO 2007/110355 A2 | 10/2007 |
| WO | WO 2009/082939 A1 | 7/2009 |

OTHER PUBLICATIONS

"Material Safety Data Sheet, Equal 65 WP (Dodine 65 WP)," Norac Concepts Inc, pp. 1-3 (Nov. 19, 2007). Retrieved from the Internet: URL:http://www.bartlett.ca/Bartlett/nmb/MSDSLabel.nsf/33679510e3c80d96852574a20055f364/0cge5ecdd7d4490385256bba006a99b3/$FILE/Equal 65WP msds english.pdf [retrieved on Sep. 21, 2011].
Dodine, "The pesticide manual ED—Worthing C R, Hance R J", Pesticide Manual. World Compendium; [Pesticide Manual], Farnham, BCPC, GB, pp. 382-383 (Jan. 1, 1995).
Pfannkoch, E. "The Preparation of Buffers and Other Solutions: A Chemist's Perspective." Molecular Biology Problem Solver: A Laboratory Guide. (c) 2001. Edited by Alan S. Gerstein.
Somers, E., et al. "Effect of Dodine Acetate on the Electrophoretic Mobility of Neurospora crassa Conidia." J. gen. Microbiol. (1967), vol. 48, pp. 147-154.
European Search Report for European Patent Application No. EP 11174573, dated Nov. 30, 2011.
International Search Report and Written Opinion for International Application No. PCT/EP2012/064237, mailed on Sep. 6, 2012.
"Fiche de Donnees de Securite," Solvesso 200, ExxonMobil, pp. 1-5 (Apr. 4, 2012).
"Pluronic® PE types," Technical Information, BASF The Chemical Company, pp. 1-16 (Mar. 2005).
International Preliminary Report on Patentability, mailed Nov. 7, 2013.

Primary Examiner — Paul V Ward
(74) Attorney, Agent, or Firm — Carmody Torrance Sandak & Hennessey LLP

(57) ABSTRACT

The current invention provides a kit of parts for producing an emulsifiable pesticide solution comprising: (a) a water miscible organic solvent selected from the list of a glycol ether, a glycerol formal, dimethylsulfoxide, gamma-butyrolactone or mixtures thereof, (b) an alkoxylated alcohol with an average of 6 to 80 moles of ethylene oxide and 2 to 60 moles of propylene oxide per mole of alcohol; and (c) a pesticidal active ingredient. The invention further provides a composition for producing an emulsifiable pesticide solution, a method for producing such a composition and a method for treating an agricultural crop. In addition the invention provides some advantageous pesticidal compositions.

21 Claims, No Drawings

METHOD FOR PRODUCING EMULSIFIABLE PESTICIDE SOLUTIONS

CROSS-REFERENCE TO RELATED APPLICATIONS

This application is the U.S. National Phase under 35 U.S.C. §371 of International Application PCT/EP2012/064237, filed Jul. 19, 2012, which claims priority to EP 11174573.3, filed Jul. 19, 2011.

TECHNICAL FIELD

The invention relates generally to the field of agricultural chemistry, and more specifically to the production of emulsifiable pesticide solutions. In particular, the invention relates to a kit of parts and to a composition suitable for the production of a wide range of pesticide emulsifiable concentrates. The invention further relates to the emulsifiable concentrates derived thereof, and to the use of the emulsions obtained from adding the emulsifiable concentrates to water for the treatment of crops. In a final aspect the invention provides a method for treating agricultural crops.

BACKGROUND

Agrochemical formulations are designed to make the product practical in use and to obtain an evenly distribution of a small amount of active substance across a wide area for treatment of an agricultural crop. When developing a formulation, a number of factors need to be taken into account: the type of application, the crop to be treated, regional variation in agronomical practice, and last but not least physical-chemical properties of the active substance, including melting point, solubility and chemical stability.

Liquid formulations are preferred by the farmer for preparing spray solutions for several reasons. They can be measured volumetrically, are easy to handle, spontaneously form stable emulsions or dispersions and, given appropriate container design, are usually easy to rinse out of the packaging. They are also easy to handle in bulk handling systems and generally do not cause application problems.

An emulsifiable concentrate consists of an active ingredient dissolved in an organic solvent, with sufficient emulsifier added to create and oil-in-water emulsion after addition of water to the emulsifiable concentrate. An emulsion is a mixture in which one liquid is suspended in another liquid. In an agrochemical emulsion, water is often the continuous phase (carrier) while oil droplets consisting of solvent plus agrochemical active ingredient, are dispersed in it.

WO 2007/017501 discloses emulsifiable concentrate formulations comprising a pesticide active ingredient multicomponent solvent system and multicomponent emulsifying system. All examples comprise an aromatic hydrocarbon mixture.

The solvent for use in an emulsifiable concentrate is selected according to its capability of solubilizing a selected active ingredient. This requirement is often fulfilled by aromatic and isoparaffinic solvents. However, the use of solvents with low flash points is becoming increasingly restricted as governmental regulations are tightening their transportation and handling. Hence, there is a need to avoid the use of flammable solvents for the solubilization of active ingredient, especially for pesticidal active ingredients.

In order produce a concentrated emulsion, the emulsifier must be carefully selected to obtain a formulation in which a selected agrochemical active ingredient is optimally distributed. To form stable concentrated emulsions, irreversible anchoring in the oil droplet and strong steric repulsion between particles are required. Irreversible flocculation, or coalescence, of the emulsions is to be prevented by creating an energy barrier that is sufficient to prevent the droplets from approaching each other closely. Steric stabilization can be produced using surfactants.

The demanding requirements outlined above result in products being developed for a specific active ingredient. This results in a large range of products in storage at a formulation plant. Whereas product development for a new formulation takes a long period of time, demand for just-in-time delivery in response to the onset diseases plant is increasing. Formulators of agrochemicals are one the one hand faced with increasing costs for raw materials and storage space, and on the other hand with increasing complexity of agrochemical formulations.

EP 1625791 discloses a liquid insecticidal composition comprising a mixture of dimethyl sulfoxide, gamma-butyrolactone and a propylene oxide/ethylene oxide block copolymer surfactant in combination with a chloronicotinyl compound.

U.S. Pat. No. 4,502,861 discloses a mothproofing formulation for application to keratinous materials comprising cypermethrin, a barbituric acid, diethylene glycol ethyl ether, amine or amide surfactant, and a block copolymer of propylene glycol and ethylene oxide.

WO 2007/017501 discloses an emulsifiable concentrate comprising a phenylsimicarbazone, a solvent system, one or more emulsifiers and optionally further formulation additives for use against insect pests.

For none of the above formulations it was disclosed whether the solvent/surfactant pair is compatible with other active ingredients, in particular with a large number of diverse pesticidal active ingredients.

There remains a need in the art for improving the manufacturing process of agrochemical products and for emulsifiable pesticide solutions, in particular for products with an improved environmental profile, that are easy to manufacture, store and use, and are economically interesting to produce.

The present invention aims to resolve or ameliorate at least some of the problems mentioned above. In particular, the invention thereto aims to provide emulsifiable pesticide solutions that are capable of reducing warehouse costs whilst not restricting the formulator of providing farmers with a broad product range of emulsifiable concentrates. The emulsifiable concentrates are capable of providing good emulsion stability over an extended period at both elevated and freezing temperatures. In addition the agrochemical formulations have a lower environmental impact and are safer in use.

SUMMARY OF THE INVENTION

The present invention thereto provides a solvent/surfactant pair suitable for combination with a large and diverse range of pesticidal active ingredients to provide emulsifiable pesticide solutions.

In a first aspect, the current invention provides a kit of parts for producing an emulsifiable pesticide solution comprising:
 (a) a water miscible organic solvent selected from the list of a glycol ether, a glycerol formal, dimethylsulfoxide, gamma-butyrolactone or mixtures thereof,
 (b) an alkoxylated alcohol with an average of 6 to 80 moles of ethylene oxide and 2 to 60 moles of propylene oxide per mole of alcohol; and
 (c) a pesticidal active ingredient.

The present invention further relates to a composition for producing emulsifiable pesticide solutions obtained from said kit comprising: a water miscible organic solvent selected from the list of a glycol ether, a glycerol formal, dimethylsulfoxide, gamma-butyrolactone or mixtures thereof; and an alkoxylated alcohol with an average of 6 to 80 moles of ethylene oxide and 2 to 60 moles of propylene oxide per mole of alcohol.

The kit of parts and composition have the advantageous effect that emulsifiable pesticide solutions can be obtained from it, in the absence of an aromatic or isoparaffinic solvent. Avoidance of these flammable solvents provides improved safety.

In a preferred embodiment of the invention, the solvent is dipropylene glycol methyl ether, diethylene glycol monoethylether or dipropylene glycol monoethyl ether.

In a preferred embodiment of the invention the alcohol alkoxylate is of formula (I) or (II), wherein x is between 2 and 22, y is between 6 and 80; and z is between 2 and 60. More preferably x is between 2 and 14, y is between 10 and 60; and z is between 2 and 45.

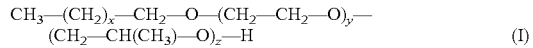

$$CH_3-(CH_2)_x-CH_2-O-(CH_2-CH_2-O)_y-(CH_2-CH(CH_3)-O)_z-H \quad (I)$$

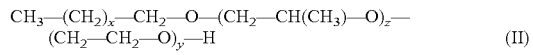

$$CH_3-(CH_2)_x-CH_2-O-(CH_2-CH(CH_3)-O)_z-(CH_2-CH_2-O)_y-H \quad (II)$$

In a preferred embodiment of the invention, the kit of parts or composition further comprise a pesticidal active ingredient selected from the list of abamectin, alpha-cypermethrin, cypermethrin, permethrin, deltamethrin, diflubenzuron, flufenoxuron, ethofenprox, malathion, pymetrozin, pyriproxifen, azoxystrobin, chlorothalonil, cyprodinil, dimethomorph, dodine, iprodione, mancozeb, metconazole, spiroxamine, 2,4-dichlorophenoxyacetic acid, 2-ethylhexyl ester (2,4-D EHE), chloroprofam (CIPC), clethodim, metribuzin, prosulfocarb, pendimethalin, triclopyr buthoxyethyl ester, trinexapac-ethyl and mixtures thereof.

In a preferred embodiment of the invention, the selected pesticidal active ingredient is a cypermethrin, an isomer of cypermethrin, or mixtures thereof; preferably the pesticidal active ingredient is cypermethrin.

The solvent/surfactant pair provided by the invention allows combination with a large and diverse range of pesticidal active ingredients to provide emulsifiable concentrates.

In a preferred embodiment of the invention, the composition comprises

| | |
|---|---|
| 25-98% | diethylene glycol monoethyl ether, |
| 1-15% | alkoxylated alcohol of formula (I), |
| 1-60% | cypermethrin, |
| 0-10% | water, and |
| 0-0.3% | antifoaming agent. |

In another preferred embodiment of the invention, the composition for producing emulsifiable pesticide solutions, comprises 250 g/l trinexapac-ethyl, 150 g/l alkoxylated alcohol of formula (I) or (II) and 550 g/l glycerol formal.

The emulsifying system of the present invention provides a system compatible with a large range of active ingredients. This is advantageous as only a limited number of water-miscible solvents and surfactants can be stored at a formulation plant, without restricting the range of commercial products that can be produced from the restricted number of raw materials. The term "surfactant" describes a compound, which can have the properties of emulsifying, dispersing or wetting agent.

In a further aspect, the invention provides a method for producing emulsifiable pesticide solutions comprising the steps of:
providing a solution comprising a water miscible organic solvent selected from the list of a glycol ether, a glycerol formal, dimethylsulfoxide, gamma-butyrolactone, or a combination thereof; and a alkoxylated alcohol with an average of 6 to 80 moles of ethylene oxide and 2 to 60 moles of propylene oxide per mole of alcohol,
adding to the solution a pesticidal active ingredient miscible with the selected solvent.

In a preferred embodiment of the method, the method comprises the step:
warming the pre-emulsion comprising the pesticidal active ingredient to a temperature between 20° C. to 60° C.

In a final aspect, the invention provides a method for treating an agricultural crop, comprising the steps of:
providing a kit of parts comprising
(a) a water miscible organic solvent selected from the list of a glycol ether, a glycerol formal, dimethylsulfoxide, gamma-butyrolactone or mixtures thereof,
(b) an alkoxylated alcohol with an average of 6 to 80 moles of ethylene oxide and 2 to 60 moles of propylene oxide per mole of alcohol; and
(c) a pesticidal active ingredient,
mixing (a) with (b) and (c) thereby providing a solution for producing emulsifiable pesticide solutions,
adding the solution to water thereby emulsifying the pesticide active ingredient and obtaining an emulsified pesticide composition comprising an active ingredient in a pre-determined dose rate,
applying the emulsified pesticide composition to an agricultural crop suffering from a disease treatable with the selected active ingredient and dose rate.

In a preferred embodiment of a method according to the invention, the active ingredient is cypermethrin or trinexapac-ethyl.

In a method according to the invention, an emulsifiable agrochemical is manufactured from a pre-emulsion comprising a combination of a solvent and surfactant, wherein this combination was found to be compatible with a large number of agrochemical active ingredients. A method according to an embodiment of the invention thus allows a reduction of the inventory at a formulation plant without having to compromise on the range of products offered to farmers. Emulsified concentrates can be manufactured on demand.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

The term "alkyl" refers to a straight or branched chain monovalent hydrocarbon radical having a specified number of carbon atoms. Alkyl groups may be unsubstituted or substituted with substituents that do not interfere with the specified function of the composition. The carbon chain length may range from 6 to 18 carbon atoms.

The term "alkoxyl" refers to a straight or branched chain monovalent hydrocarbon radical having a specified number of carbon atoms and a carbon-oxygen-carbon bond, may be unsubstituted or substituted with substituents that do not interfere with the specified function of the composition.

The term "non-ionic" refers to a surface active compound, i.e. a surfactant, with one or more uncharged hydrophilic substituents that does not generally dissociate as ions in a solution, distinguishable from anionic and cationic surfactants. The non-ionic surfactants are primarily organic compounds having both hydrophilic and hydrophobic moieties.

The inventors have found a composition which can act as a pre-emulsion for a large number of agrochemical active ingredients. The composition comprises a water miscible organic solvent and a non-ionic surfactant.

The organic solvent is selected from the list of a glycol ether, a glycerol formal, dimethylsulfoxide, gamma-butyrolactone or a combination thereof.

By the term "a glycol ether" as used herein, it is meant a compound formed from a reaction of alkylene oxide with alcohols like methanol, ethanol, propanol, butanol or phenol. Subsequent reaction with additional alkylene oxide leads to corresponding di-, tri- and higher glycol ethers. The reaction is typically catalyzed by a base.

Glycol ethers can be represented by the structural formula [CH3-CH2(OH)—CH2-O]n-R, wherein n=1, 2, or 3; and R=alkyl, preferably methyl, ethyl, propyl or butyl.

Examples of ethylene glycol ethers are ethylene glycol monomethyl ether (2-methoxyethanol, $CH_3OCH_2CH_2OH$), ethylene glycol monoethyl ether (2-ethoxyethanol, $CH_3CH_2OCH_2CH_2OH$), ethylene glycol monopropyl ether (2-propoxyethanol, $CH_3CH_2CH_2OCH_2CH_2OH$), ethylene glycol monoisopropyl ether (2-isopropoxyethanol, $(CH_3)_2CHOCH_2CH_2OH$), ethylene glycol monobutyl ether (2-butoxyethanol, $CH_3CH_2CH_2CH_2OCH_2CH_2OH$), ethylene glycol monophenyl ether (2-phenoxyethanol, $C_6H_5OCH_2CH_2OH$), ethylene glycol monobenzyl ether (2-benzyloxyethanol, $C_6H_5CH_2OCH_2CH_2OH$), diethylene glycol monomethyl ether (2-(2-methoxyethoxy)ethanol, methyl carbitol, $CH_3OCH_2CH_2OCH_2CH_2OH$), diethylene glycol monoethyl ether (2-(2-ethoxyethoxy)ethanol, carbitol cellosolve, $CH_3CH_2OCH_2CH_2OCH_2CH_2OH$) and diethylene glycol mono-n-butyl ether (2-(2-butoxyethoxy)ethanol, $CH_3CH_2CH_2CH_2OCH_2CH_2OCH_2CH_2OH$).

Diethylene glycol monoethyl ether is commercially available under the trade name Carbitol.

Examples of propylene glycol ethers are propylene glycol n-butyl ether, dipropylene glycol n-butyl ether, dipropylene glycol methyl ether acetate, tripropylene glycol methyl ether, propylene glycol methyl ether, propylene glycol methyl ether acetate, dipropylene glycol methyl ether, propylene glycol n-butyl ether, dipropylene glycol n-butyl ether, dipropylene glycol methyl ether acetate and tripropylene glycol methyl ether.

In a preferred embodiment of a composition of the invention, the solvent is dipropylene glycol methyl ether or diethylene glycol methyl ether.

Dipropylene glycol methyl ether is commercially available under the trade name Dowanol DPM from the company Dow, US. Dipropylene glycol is a hydrophilic glycol ether with 100% water solubility at a temperature of 25° C. It has a mid- to slow evaporating rate. For example, Dowanol DPM has a relative evaporation rate of 0.03 (based on an arbitrary evaporation rate of butyl acetate of 1.0). It may be represented by the formula $CH_3O[CH_2CH(CH_3)O]_2H$ (one of several isomers).

By the term "a glycerol formal" as used herein, it is meant a composition consisting of 5-hydroxy-1,3-dioxane and 4-hydroxymethyl-1,3-dioxolane, typically in a ratio of 60:40. It is prepared from glycerin and formaldehyde. The boiling point of glycerol formal is 191-195° C. at 760 mm Hg. Glycerol formal provides an environmentally-friendly alternative to aromatic solvents.

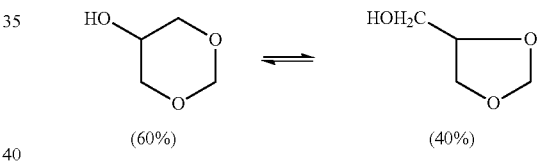

(60%)    (40%)

Dimethyl sulfoxide (DMSO) I san organosulfur compound with formula $(CH_3)_2SO$. This colorless liquid is an important polar aprotic solvent that is capable of dissolving both polar and nonpolar compounds. It is miscible in a wide range of organic solvents as well as water.

Gamma-butyrolactone, abbreviated GBL, is a hygroscopic colorless oily liquid which is soluble in water.

In another preferred embodiment the solvent is a 40:60 mixture of dimethylsulfoxide and gammabutyrolactone. By the term "a 40:60 mixture of dimethylsulfoxide and gamma-butyrolactone" as used herein, it is meant a composition essentially comprising dimethylsulfoxide and gamma-butyrolactone in a ratio of 40 weight % dimethylsulfoxide to 60 weight % gamma-butyrolactone.

These solvents are non-flammable, relatively cheap, easily pourable as of low viscosity, and of improved toxicological profile.

The inventors have found that a composition comprising a water miscible organic solvent selected from the list of a propylene glycol ether, a glycerol formal, dimethylsulfoxide, gamma-butyrolactone or a mixture thereof; and an alcohol alkoxylate derived from ethylene/propylene oxide units, is particularly advantageous for producing emulsifiable pesticide solutions. This combination of solvent and non-ionic surfactant was found to be compatible with a large range of pesticidal active ingredients.

Preferably the alkoxylated alcohol has an alkyl chain length of at least 4 carbon atoms, preferably of 4 to 24 carbon atoms, more preferably of 4 to 16 carbon atoms, most preferably of 12 to 15 carbon atoms. The alkoxylated alcohol is preferably an alkoxylated fatty alcohol, meaning the alcohol part has a carbon chain length of at least 8 carbon atoms.

The alkoxylated alcohol preferably has an average of 10 to 60 moles of ethylene oxide and 2 to 45 moles of propylene oxide per mole of alcohol; preferably 4 to 40 moles of propylene oxide per mole of alcohol.

The alkoxylated alcohol is preferably a block ethylene oxide/propylene oxide adduct. More preferably the alkoxylated alcohol is a fatty alcohol/ethylene oxide/propylene oxide adduct.

Preferably the alkoxylated alcohol is a tri-block copolymer of fatty alcohol/ethylene oxide/propylene oxide or fatty alcohol/propylene oxide/ethylene oxide of general formula (I) or (II)

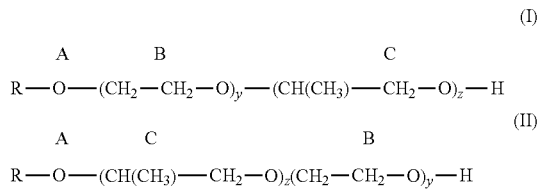

wherein A is an alcohol moiety, R is a hydrocarbon chain of from 4 to 24 carbon atoms, B represents ethylene oxide units and C represents propylene oxide units. The hydrophobic moiety R of the nonionic compound may be a primary or secondary, straight or branched alcohol having from 4 to 24 carbon atoms. Preferably the number of carbon atoms in R is at least 4, preferably between 4 and 15. R represents CH3-(CH2)x- Preferably x is between 3 and 14. y and z represent the average degree of ethoxylation and propoxylation, respectively of 6 to 80 and 2 to 60. Preferably y is between 10 and 60, and z is between 2 and 45; preferably between 4 and 40.

The compounds represented by formula (I) and (II) can be obtained by the reaction of an alcohol with ethylene oxide and propylene oxide. Ethoxylations and propoxylations of alcohols are processes known to a person skilled in the art.

The alcohol alkoxylate of formula (I) or (II), can be derived from an alcohol described as ROH, wherein R is $CH_3-(CH_2)_x-CH_2-$ and x is between 2 and 22. The alcohol may be butanol, hexanol, octanol, or a fatty alcohol. Alkoxylation is preferably achieved by ethoxylation and propoxylation.

The compound of formula (I) and (II) is preferably an alkoxylated fatty alcohol, more preferably an ethyoxylated and propoxylated block co-polymer, more preferably an ethoxylated and propoxylated block co-polymer of a fatty alcohol with carbon chain length of at least 4, preferably 4 to 15. Most preferably the compound of formula I is a reaction product of a fatty alcohol with carbon chain length of at least 4, preferably between 12 and 15, with 2 to 45 moles of propylene oxide and 10 to 60 moles of mole ethylene oxide.

They may be obtained by condensation of an alcohol containing from 4 to 16 carbon atoms in a straight or branched chain configuration, condensed with 10 to 60 moles of ethylene oxide and with 2 to 45 moles of propylene oxide.

Most preferably the compound alkoxylated alcohol is a tri-block copolymer of structure ABC or ACB, wherein A is the fatty alcohol, B is polyethylene oxide and C is polypropylene oxide.

Preferably the minimum number average molecular weight of the alkoxylated alcohol, expressed in atomic mass units, is at least 1000, more preferably at least 1500, most preferably at least 2500.

Suitable ethoxylated/propoxylated fatty alcohols for use in the invention may be commercially available in the product range under the trade name Antarox, available from Rhodia; Surfonic LF, available from Huntsman; Tergitol XD available from Dow; Synperonic PE, available from BASF; Atlas G5000, available from Uniqema; Dehypon, available from Cognis; Tensiofix UNI01 and Tensiofix AGCA22 available from Ajinomoto Omnichem.

More preferably the alkoxylated alcohol are α-alkyl-ω-hydroxypoly (oxypropylene) and poly (oxyethylene) polymers where the alkyl chain contains a minimum of four carbons and the minimum number average molecular weight, expressed in atomic mass units, is 1100.

Most preferably the alkoxylated alcohol are α-alkyl ($C_{12}$-$C_{15}$)-ω-hydroxypoly(oxypropylene)poly(oxyethylene)co-polymers, wherein the poly(oxypropylene) content is 3-60 moles and the poly(oxyethylene) content is 5-80 moles, the resulting ethoxylated propoxylated ($C_{12}$-$C_{15}$) alcohols having a minimum molecular weight, expressed in atomic mass units of 1500. Such a product can be represented with the formula $CH_3-(CH_2)_{10-13}-CH_2-O-(CH_2-CH_2-O)_{3-60}-(CH(CH_3)-CH_2-O)_{5-80}-H$. An example is represented by the compound with chemical abstract number CAS 68551-13-3.

A composition according to an embodiment of the invention is compatible with a broad range of pesticide active ingredients. This allows reducing the number of formulations and raw materials that have to be kept in stock in order to be able to manufacture a broad range of emulsifiable concentrates. This is cost effective.

The emulsifying system of the present invention is advantageous in that only few types of solvent miscible to water and surfactant need to be kept in stock at the production plant, allowing the manufacturing of a large range of commercial products with a restricted number of raw materials.

By the term "compatible" as used herein, it is meant herein that no adverse effects occur as a result of mixing them together. An incompatible mix can cause equipment damage, downtime, damage to desirable plants and chemical ineffectiveness. Incompatible mixes can result from chemical or physical incompatibility. Chemical incompatibility occurs when one or more of the chemicals changes properties. Physical incompatibility causes the formation of lumps or gels. The chemicals do not disperse properly and settle out of suspension. Incompatibility can also take the form of foams, stratification in the tank, colour changes and bubbles.

By the term "active ingredient" as used herein, is meant an ingredient that is chemically active and/or biologically active in origin. The activity is directed against a pest, particularly a plant pest. In this regard an "active ingredient" ingredient can be a single ingredient or a combination of ingredients.

Active ingredients suitable for use in the present invention include insecticides such as abamectin, alpha-cypermethrin, cypermethrin, permethrin, deltamethrin, diflubenzuron, flufenoxuron, ethofenprox, malathion, pymetrozin, pyriproxifen, azoxystrobin, chlorothalonil, cyprodinil, dimethomorph, dodine, iprodione, mancozeb, metconazole, spiroxamine, 2,4-dichlorophenoxyacetic acid, 2-ethylhexyl ester (2,4-D EHE), chloroprofam (CIPC), clethodim, metribuzin, prosulfocarb, pendimethalin, triclopyr buthoxyethyl ester, and trinexapac-ethyl.

In a preferred embodiment of the composition, the composition further comprises a pesticidal active ingredient selected from the list of abamectin, chlorpyriphos ethyl, a cypermethrin, deltamethrin, diflubenzuron, fenoxycarb, indoxacarb, malathion, pymetrozin, pyriproxifen; azoxystrobin, captan, chlorothalonil, cyprodinil, dimethomorph, dodine, folpet, fosetyl-aluminium, iprodione, mancozeb, metconazole, spiroxamine, 2,4-dichlorophenoxyacetic acid (2,4-D acid), 2,4-dichlorophenoxyacetic acid, 2-ethylhexyl ester (2,4-D EHE), chloroprofam (CIPC), clethodim, glyphosate, 2-methyl-4-chlorophenoxyacetic acid (MCPA), metribuzin, prosulfocarb, pendimethalin, triclopyr, gibberellic acid, maleic hydrazide and trinexapac-ethyl.

In a preferred embodiment of the invention, the active ingredient is trinexapac-ethyl. This has for effect that solution will not freeze at a temperature of 4 to 5° C.

In a preferred embodiment, the composition comprising trinexapac-ethyl as active ingredient is as follows:
Trinexapac-ethyl: 250 g/l
Tensiofix UNI 1: 150 g/l
Tensiofix D03: 200 g/l
Surfynol DF58: 2 g/l
Glycerol formal: 550 g/l
The Tensiofix D03 surfactant acts as biological activator. This surfactant is not necessary for the emulsion stability.

In a preferred embodiment of the composition, the selected pesticidal active ingredient is a cypermethrin. By the term "a cypermethrin" as used herein it is meant, alpha-cypermethrin, cypermethrin, beta-cypermethrin, zeta-cypermethrin; and mixtures, derivatives or isomers thereof.

Cypermethrin is the ISO approved common name for (RS)-α-cyano-3-phenoxybenzyl (1RS,3RS;1RS,3SR)-3-(2,2-dichlorovinyl)-2,2-dimethyl cyclo propane carboxylate. Cypermethrin is a synthetic pyrethroid insecticide containing three chiral centers, giving a racemic mixture of eight isomers comprising four diasterioisomeric pairs.

Alpha cypermethrin is a racemate consisting essentially of two of the four cis isomers comprised in cypermethrin, in particular (S)-alpha-cyano-3-phenoxybenzyl (1R,3R)-3-(2,2-dichlorovinyl)-2,2-dimethylcyclopropane carboxylate and (R)-alpha-cyano-3-phenoxybenzyl (1S,3S)-3-(2,2-dichlorovinyl)-2,2-dimethylcyclopropane carboxylate.

Beta cypermethrin contains 4 of the 8 isomers which constitute cypermethrin. The isomers in beta-cypermethrin include 2 cis isomers (1S-cis-R and 1R-cis-S), which are the isomers contained in alpha-cypermethrin and 2 trans isomers (1S-trans-R and 1R-trans-S). The cis isomers have a greater insecticidal activity than the trans isomers.

The term "zeta-cypermethrin" as used herein means (R,S)-α-cyano-3-phenoxybenzyl-(1RS)-cis-trans-3-(2,2-dichlorovinyl)-2,2-dimethylcyclo propane carboxylate.

In a more preferred embodiment of the invention, the selected pesticidal active ingredient is cypermethrin.

In a more preferred embodiment of the invention, the selected pesticidal active ingredient is cypermethrin, the surfactant is an alkoxylated alcohol of formula (I) or (II) and the solvent is diethylene glycol monoethyl ether.

Examples of such alcohols particularly include primary alcohols, which may be linear or branched, particularly mono-branched. The alkoxylation parts such alcohols are mixed ethoxylated/propoxylates which may be block or random mixed alkoxylates, typically containing from 6 to 80 moles of ethylene oxide and from 2 to 60 of propylene oxide, preferably where the polyalkoxylate chain is terminated with propylene oxide units. Preferably the polyoxyethylene/polyoxypropylene copolymers are block copolymers.

A preferred embodiment of the invention is a pesticidal composition wherein cypermethrin is present in an amount of 1% to 60%, the alkoxylated alcohol of formula (I) is present in an amount of 1%-20%, and diethylene glycol monoethyl ether is present in an amount of 25%-98%, wherein all the percentages are % by weight based upon the total weight of all the components in the composition. In addition the composition may comprise 0% to 10% water. An antifoaming agent may be present in the composition, in an amount of 0% to 0.3%.

In a preferred embodiment of the composition, the composition comprises:
50 wt % cypermethrin,
35% diethylene glycol monoethyl ether,
14.9 wt % alcohol/ethylene oxide/propylene oxide triblock copolymer, and 0.1% antifoaming agent.

In a preferred embodiment, the composition has a pH between 1 and 13, preferably the composition has a pH between 4 to 8, more preferably the pH of the composition is around 6.

The emulsifying system of the present invention provides a system compatible with a large range of active ingredients. This is advantageous as only a limited number of water-miscible solvents and surfactants can be stored at a formulation plant, without restricting the range of commercial products that can be produced from the restricted number of raw materials.

In a further aspect, the invention provides a method for the preparation of an emulsifiable pesticide solution and of an emulsified pesticide composition derived thereof.

A method according to an embodiment of the invention for producing emulsifiable pesticide solutions comprises the step of:
  selecting a water miscible organic solvent from the list of a glycol ether, a glycerol formal, dimethylsulfoxide, gamma-butyrolactone, or mixtures thereof,
  charging the solvent to a blending vessel,
  adding to the selected solvent an alcohol alkoxylate of formula (I), wherein x is between 2 and 14, y is between 6 and 80, and z is between 2 and 60,
  mixing the solvent and alcohol alkoxylate to obtain a pre-emulsion for a pesticide active ingredient.

By the term "pre-emulsion" as used herein is meant, a composition suitable for the production of a pesticide emulsifiable concentrate.

The selection of the solvent is directed to the solubility of the active ingredient in the solvent.

The composition obtained as described above may serve as a solvent/surfactant pair for a broad range of pesticide active ingredients. To obtain a emulsifiable pesticide solution, a pesticidal active ingredient miscible with the selected solvent/surfactant pair is added to the pre-emulsion. The miscibility can be checked with a standard solubility screening test, known to a person skilled in the art. The emulsifiable pesticide solution thus obtained may be stored prior to its use for obtaining an emulsified pesticide solution.

The mixing can be carried out at room temperature or preferably at an elevated temperature. In a preferred embodiment of the method, the method comprises the step of warming the solution comprising the pesticidal active ingredient to a temperature between 20° C. to 60° C., preferably between 30° C. to 60° C.; more preferably around 40° C. Warming the mixture to a temperature of about 40° C. facilitates the dissolution of the pesticide.

In a preferred embodiment of the method, the method comprises the step of adding the emulsifiable composition to water thereby obtaining an emulsified pesticide composition, and applying the emulsified pesticide composition to an agricultural crop for the treatment of a pest treatable with the selected active ingredient.

The pesticide active ingredients may be used in the form of liquids or powders. After mixing with the emulsifying system of the invention are pourable emulsifiable formulations which are readily dispersible in water. The resulting emulsions are stable over time, typically in the order of at least 4 hours. The finished product is not yet emulsified. When it is diluted with water, the emulsifiable composition will form the emulsion. The emulsion is stable for at least 4 hours.

The pesticidal composition according to the invention is prepared by mixing the solvent miscible with the pesticidal composition at concentration ranging from 10 g/l for the lowest concentration (for instance in case of cypermethrin) until 800 g/l for the highest concentration (for instance in case of triclopyr buthoxyethyl ester).

In a preferred embodiment a composition of the invention is used for the treatment of agricultural crops.

In a final aspect, the invention provides a method for treating an agricultural crop, comprising the steps of:
providing a kit of parts comprising
(a) a water miscible organic solvent selected from the list of a glycol ether, a glycerol formal, dimethylsulfoxide, gamma-butyrolactone or mixtures thereof,
(b) an alkoxylated alcohol with an average of 6 to 80 moles of ethylene oxide and 2 to 60 moles of propylene oxide per mole of alcohol; and
(c) a pesticidal active ingredient,
mixing (a) with (b) and (c) thereby providing a solution for producing emulsifiable pesticide solutions,
adding water to the solution thereby emulsifying the pesticide active ingredient and obtaining an emulsified pesticide composition comprising an active ingredient in a pre-determined dose rate,
applying the emulsified pesticide composition to an agricultural crop suffering from a disease treatable with the selected active ingredient and dose rate.

In a preferred embodiment the kit of parts is accompanied with an information leaflet providing instructions to combine the solvent, surfactant and pesticidal active ingredient to obtain an emulsifiable pesticide solution. The product leaflet may specify the concentrations of the ingredients to be used. It may also provide specific examples of compositions.

The present invention will be now described in more details, referring to examples that are not limitative. It is supposed that the present invention is not restricted to any form of realization described previously and that some modifications can be added to the presented example of fabrication without reappraisal of the appended claims.

EXAMPLES

Example 1

In the experiment summarized in Table 1, emulsifiable pesticide solutions were prepared starting from a kit of parts comprising DMSO 40%+GBL 60%, Tensiofix UNI01 and a selection out of a group of active ingredients. First, the solvent DMSO40/GBL60 was mixed with a non-ionic surfactant, in particular with Tensiofix UNI01. The mixture obtained was divided into several samples. To the samples a selected active ingredient was added. The emulsifiable pesticide solution thus obtain was inspected for emulsion stability. It was observed if a homogenous mixture was obtained and if no visible amounts of pesticide settled.

TABLE 1

Summary of experiment of Example 1

| Active ingredient (g/l) | | Surfactant (g/l) | | Solvent | | Emulsion 1% v/v CIPAC D water 20° C. |
|---|---|---|---|---|---|---|
| Difenoconazole | 250 | Tensiofix UNI01 | 150 | Mix GBL/DMSO 40/60 | to 1 L | no oily phase |
| Imazalil | 100 | Tensiofix UNI01 | 150 | Mix GBL/DMSO 40/60 | to 1 L | no oily phase |
| Triclopyr | 800 | Tensiofix UNI01 | 100 | Mix GBL/DMSO 40/60 | to 1 L | no oily phase |
| Prosulfocarb | 500 | Tensiofix UNI01 | 100 | Mix GBL/DMSO 40/60 | to 1 L | no oily phase |
| CIPC | 100 | Tensiofix UNI01 | 150 | Mix GBL/DMSO 40/60 | to 1 L | no oily phase |
| Cypermethrin + PBO | 60 + 171 | Tensiofix UNI01 | 150 | Mix GBL/DMSO 40/60 | to 1 L | no oily phase |
| Trinexapac-ethyl | 250 | Tensiofix UNI01 | 150 | Mix GBL/DMSO 40/60 | to 1 L | no oily phase |
| Pyriproxifen | 100 | Tensiofix UNI01 | 150 | Mix GBL/DMSO 40/60 | to 1 L | no oily phase |
| Permethrin | 250 | Tensiofix UNI01 | 150 | Mix GBL/DMSO 40/60 | to 1 L | no oily phase |

In Examples 2 to 4 further examples of emulsifiable compositions are provided. To obtain an emulsion concentrate, water is added to the composition.

Example 2

Cypermethrin: 50%
Tensiofix UNI01: 14.9%
Surfynol DF58 (antifoam): 0.1%
Carbitol: 35%

Example 3

Cypermethrin: 10%
Dowanol DPM: 82%
Tensiofix UNI01: 4%
Water: 4%

Example 4

Spiroxamine: 50%
Dowanol DPM: 35%
Tensiofix UNI01: 15%

Example 5

In the following experiment pesticidal compositions were prepared comprising different solvent surfactant pairs. These include solvent/surfactant pairs according to the invention (Refs 2-4) and others. The respective compositions are provided in the columns active ingredient/surfactant/solvent/other. The amount of ingredients used is also indicated. After constitution of the formulas, the aspect of the final product was visually observed and noted down. The result is reflected in the column final product aspect. The formulations were used to prepare emulsions as in previous examples, 1% v/v. After 1 hour the 1% emulsions were again observed and the result noted down in the column emulsion stability. The results were photographed.

Pluronic PE 10400 is an EO/PO block co-polymer, in particular an ABA block co-polymer containing 25 moles of ethylene oxide, 56 moles of propylene oxide and 25 moles of ethylene oxide providing the chemical structure $EO_{25}PO_{56}EO_{25}$.

Synperonic PE/P105 is an EO/PO block co-polymer, in particular, an ABA block-co-polymer containing 37 moles of ethylene oxide (EO), 56 moles of propylene oxide (PO) and 37 moles of ethylene oxide (EO) providing the chemical structure $EO_{37}PO_{56}EO_{37}$.

Genapol EP 0244 is an alcohol alkoxylate, in particular a C10/C12 alcohol with 4 EO followed by 4 PO.

Tensiofix UNI01 is an alcohol alkoxylate with an average of 6 to 80 moles of ethylene oxide and 4 to 60 moles of propylene oxide per mole of alcohol.

As can be seen from the results reported in Tables 2-4, formulas with a solvent/surfactant pair according to the invention provided homogeneous and stable emulsions. Formation of sediment was not observed after 1 hour in CIPAC D water at 20° C.

For other solvent/surfactant pairs, wherein the solvent was kept the same and the surfactant was similar, a homogenous emulsion without sediment formation or crystallization could not be obtained.

TABLE 2 comparative examples of emulsifiable cypermethrin solutions, and emulsions obtainable thereof

| Formula | Active ingredient | g/l | Surfactant | g/l | Solvent | g/l | Other | g/l | Final product aspect | Self emulsification | Emulsion 1% v/v - stability after 1 hour in CIPAC D water at 20° C. |
|---|---|---|---|---|---|---|---|---|---|---|---|
| 4 | Cypermethrin technical grade | 500 | Pluronic PE 10400 | 149 | Carbitol | To 1 L | Surfynol DF58 | 1 | Limpid liquid Dark yellow | Homogeneous | 0.5 ml sediment in the bottom |
| 5 | Cypermethrin technical grade | 500 | Genapol EP 0204 | 149 | Carbitol | To 1 L | Surfynol DF58 | 1 | Limpid liquid Dark yellow | Non-homogeneous | Formula has agglomerate in the bottom Suspended agglomerates |
| 6 | Cypermethrin technical grade | 500 | Synperonic PE/P 105 | 149 | Carbitol | To 1 L | Surfynol DF58 | 1 | Limpid liquid Yellow | Non-homogeneous | 0.5 ml of sediment |
| Ref 2 (embodiment invention) | Cypermethrin technical grade | 500 | Tensiofix UNI 01 | 149 | Carbitol | To 1 L | Surfynol DF58 | 1 | Limpid liquid Pale yellow | Homogeneous | Homogeneous |

TABLE 3 comparative examples of prosulfocarb solutions, and emulsions obtainable thereof

| Formula | Active ingredient | g/l | Surfactant | g/l | Solvent | g/l | Final product aspect | Self emulsification | Emulsion 1% v/v - stability after 1 hour in CIPAC D water at 20° C. |
|---|---|---|---|---|---|---|---|---|---|
| 7 | Prosulfocarb Technical grade | 500 | Pluronic PE 10400 | 100 | GBL40/DMSO 60 | To 1 L | Limpid liquid Light yellow | Non-homogeneous Flakes | 2 ml sediment |
| 8 | Prosulfocarb Technical grade | 500 | Genapol EP0204 | 100 | GBL40/DMSO 60 | To 1 L | Limpid liquid Light yellow | Non-homogeneous Oily spheres going down | Non-homogeneous |
| 9 | Prosulfocarb Technical grade | 500 | Synperonic PE/P 105 | 100 | GBL40/DMSO 60 | To 1 L | Limpid liquid Light yellow | Non-homogeneous | 1.7 ml sediment |
| Ref 3 (embodiment invention) | Prosulfocarb Technical grade | 500 | Tensiofix UNI01 | 100 | GBL40/DMSO 60 | To 1 L | Limpid liquid Yellow | Homogeneous | Homogenous |

TABLE 4 comparative examples of emulsifiable pyriproxifen solutions, and emulsions obtainable thereof

| Formula | Active ingredient | g/l | Surfactant | g/l | Solvent | g/l | Final product aspect | Self emulsification | Emulsion 1% v/v - stability after 1 hour in CIPAC D water at 20° C. |
|---|---|---|---|---|---|---|---|---|---|
| 10 | Pyriproxifen Technical grade | 100 | Pluronic PE 10400 | 100 | GBL40/DMSO 60 | To 1 L | Limpid liquid Colourless | Homogeneous | 3 ml sediment |
| 11 | Pyriproxifen Technical grade | 100 | Genapol EP0204 | 100 | GBL40/DMSO 60 | To 1 L | Limpid liquid Colourless | Homogeneous | Small crystals on the bottom |
| 12 | Pyriproxifen Technical grade | 100 | Synperonic PE/P 105 | 100 | GBL40/DMSO 60 | To 1 L | Limpid liquid Colourless | Homogeneous | 1.8 ml sediment |
| Ref 4 (embodiment invention) | Pyriproxifen Technical grade | 100 | Tensiofix UNI01 | 100 | GBL40/DMSO 60 | To 1 L | Limpid liquid Colourless | Homogeneous | Homogenous |

What is claimed is:

1. Kit of parts for producing an emulsifiable pesticide solution comprising:
   (a) a water miscible organic solvent selected from the group consisting of a glycol ether, a glycerol formal, dimethylsulfoxide, gamma-butyrolactone and mixtures thereof,
   (b) an alkoxylated alcohol having an alkyl chain length of 4 to 24 carbon atoms with an average of 6 to 80 moles of ethylene oxide and 2 to 60 moles of propylene oxide per mole of alcohol; and
   (c) a pesticidal active ingredient,
   wherein the alkoxylated alcohol is of formula (I) or (II),

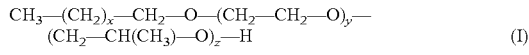

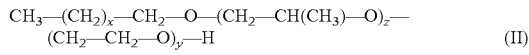

and wherein the alcohol part has a carbon chain length of at least 8 carbons, y is between 6 and 80; and z is between 2 and 60; with the proviso that an aromatic or isoparaffinic solvent are absent.

2. Composition for producing emulsifiable pesticide solutions, obtained from a kit of parts according to claim 1, comprising:
   (a) a water miscible organic solvent selected from the group consisting of a glycol ether, a glycerol formal, dimethylsulfoxide, gamma butyrolactone and mixtures thereof; and
   (b) an alkoxylated alcohol having an alkyl chain length of 4 to 24 carbon atoms with an average of 6 to 80 moles of ethylene oxide and 2 to 60 moles of propylene oxide per mole of alcohol,
   wherein the alkoxylated alcohol is of formula (I) or (II),

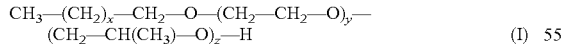

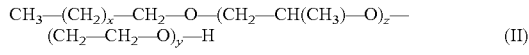

and wherein the alcohol part has a carbon chain length of at least 8 carbons, y is between 6 and 80; and z is between 2 and 60; with the proviso that an aromatic or isoparaffinic solvent are absent.

3. Composition according to claim 2, wherein the solvent is dipropylene glycol methyl ether, diethylene glycol monoethylether or dipropylene glycol monoethyl ether.

4. Composition according to claim 2, wherein y is between 10 and 60; and z is between 2 and 45.

5. Composition according to claim 2, wherein the pesticidal active ingredient is selected from the group consisting of abamectin, alpha-cypermethrin, cypermethrin, permethrin, deltamethrin, diflubenzuron, flufenoxuron, ethofenprox, malathion, pymetrozin, pyriproxifen, azoxystrobin, chlorothalonil, cyprodinil, dimethomorph, dodine, iprodione, mancozeb, metconazole, spiroxamine, 2,4-dichlorophenoxyacetic acid, 2-ethylhexyl ester (2,4-D EHE), chloroprofam (CIPC), clethodim, metribuzin, prosulfocarb, pendimethalin, triclopyr buthoxyethyl ester, trinexapac-ethyl, and a mixture thereof.

6. Composition according to claim 2, wherein the selected pesticidal active ingredient is cypermethrin, an isomer of cypermethrin, or mixtures thereof.

7. Composition according to claim 6, wherein the pesticidal active ingredient is cypermethrin.

8. Composition according to claim 2, wherein the selected pesticidal active ingredient is trinexapac-ethyl.

9. Composition according to claim 7, comprising:

| | |
|---|---|
| 25-98% | diethylene glycol monoethyl ether, |
| 1-20% | alkoxylated alcohol, |
| 1-60% | cypermethrin, |
| 0-10% | water, and |
| 0-0.3% | antifoam. |

10. Composition for producing emulsifiable pesticide solutions, comprising
    250 g/l trinexapac-ethyl
    150 g/l alkoxylated alcohol as described in claim 2, and
    550 g/l glycerol formal.

11. Method for producing emulsifiable pesticide solutions comprising the steps of:
    providing a solution of a water miscible organic solvent wherein the water miscible organic solvent is selected from the group consisting of a propylene glycol ether, a glycerol formal, a dimethylsulfoxide and gamma-butyrolactone and a mix thereof; and an alkoxylated alcohol having an alkyl chain length of 4 to 24 carbon atoms with an average of 6 to 80 moles of ethylene oxide and 2 to 60 moles of propylene oxide per mole of alcohol, and
    adding to the solution a pesticidal active ingredient miscible with the selected solvent, wherein the alkoxylated alcohol is of formula (I) or (II),

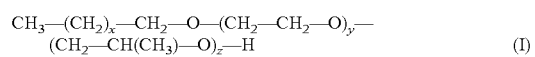

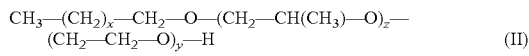
(II)

And wherein the alcohol part has a carbon chain length of at least 8 carbon atoms, y is between 6 and 80; and z is between 2 and 60; with the proviso that an aromatic or isoparaffinic solvent are absent.

12. Method according to claim 11, further comprising the step:
warming the solution comprising the pesticidal ingredient to a temperature between 20° C. to 60° C.

13. Method for treating an agricultural crop, comprising the steps of:
providing a kit of parts comprising:
(a) a water miscible organic solvent selected from the group consisting of a glycol ether, a glycerol formal, dimethylsulfoxide, gamma-butyrolactone and mixtures thereof,
(b) an alkoxylated alcohol having an alkyl chain length of 4 to 24 carbon atoms with an average of 6 to 80 moles of ethylene oxide and 2 to 60 moles of propylene oxide per mole of alcohol; and
(c) a pesticidal active ingredient,
wherein the alkoxylated alcohol is of formula (I) or (II),

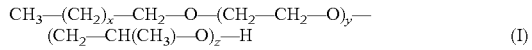
(I)

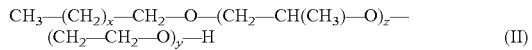
(II)

and wherein the alcohol part has a carbon chain length of at least 8 carbons, y is between 6 and 80; and z is between 2 and 60; with the proviso that an aromatic or isoparaffinic solvent are absent,
mixing (a) with (b) and (c) thereby providing a solution for producing emulsifiable pesticide solutions,
adding water to the solution thereby emulsifying the pesticide active ingredient and obtaining an emulsified pesticide composition comprising an active ingredient in a pre-determined dose rate, and
applying the emulsified pesticide composition to an agricultural crop suffering from a disease treatable with the selected active ingredient and dose rate.

14. Method according to claim 11, wherein the active ingredient is cypermethrin or trinexapac-ethyl.

15. Method according to claim 13, wherein the active ingredient is cypermethrin or trinexapac-ethyl.

16. Kit of parts according to claim 1, wherein the solvent is dipropylene glycol methyl ether, diethylene glycol monoethylether or dipropylene glycol monoethyl ether.

17. Kit of parts according to claim 1, wherein y is between 10 and 60; and z is between 2 and 45.

18. Kit of parts according to claim 1, wherein the pesticidal active ingredient is selected from the group consisting of abamectin, alpha-cypermethrin, cypermethrin, permethrin, deltamethrin, diflubenzuron, flufenoxuron, ethofenprox, malathion, pymetrozin, pyriproxifen, azoxystrobin, chlorothalonil, cyprodinil, dimethomorph, dodine, iprodione, mancozeb, metconazole, spiroxamine, 2,4-dichlorophenoxyacetic acid, 2-ethylhexyl ester (2,4-D EHE), chloroprofam (CIPC), clethodim, metribuzin, prosulfocarb, pendimethalin, triclopyr buthoxyethyl ester, trinexapac-ethyl, and a mixture thereof.

19. Kit of parts according to claim 1, wherein the selected pesticidal active ingredient is a cypermethrin, an isomer of cypermethrin, or mixtures thereof.

20. Kit of parts according to claim 19, wherein the pesticidal active ingredient is cypermethrin.

21. Kits of parts according to claim 1, wherein the selected pesticidal active ingredient is trinexapac-ethyl.

* * * * *